United States Patent [19]

Umekawa

[11] Patent Number: 5,017,592
[45] Date of Patent: May 21, 1991

[54] STABLE BIOCIDE COMPOSITION FOR INDUSTRIAL USE

[76] Inventor: Osamu Umekawa, 756-26, Nagose, Kaizuka-shi, Osaka 597, Japan

[21] Appl. No.: 443,124

[22] Filed: Nov. 30, 1989

[30] Foreign Application Priority Data

Dec. 12, 1988 [JP] Japan .................................. 63-313270

[51] Int. Cl.$^5$ ............................................ A01N 43/80
[52] U.S. Cl. .................................. 514/372; 106/18.22
[58] Field of Search .................. 514/372; 424/272; 106/18.22

[56] References Cited

U.S. PATENT DOCUMENTS 3,870,795  3/1975  Miller et al. .......................... 514/372
4,661,503  4/1987  Martin et al. ......................... 514/372
4,783,221  11/1988  Grove .............................. 106/18.22

FOREIGN PATENT DOCUMENTS 60-1105  1/1985  Japan .

OTHER PUBLICATIONS

Chemical Abstracts (vol. 102, p. 199590v) 1985.

Primary Examiner—Stanley J. Friedman
Assistant Examiner—Kevin Weddington
Attorney, Agent, or Firm—Wenderoth, Lind & Ponack

[57] ABSTRACT

A stable biocide composition for industrial use which comprises 4,5-dichloro-1,2-dithiol-3-one and a mixture of 5-chloro-2-methyl-3-isothiazolone and 2-methyl-3-isothiazolone, together with a substantially anhydrous organic solvent for dissolving said ingredients.

5 Claims, No Drawings

STABLE BIOCIDE COMPOSITION FOR INDUSTRIAL USE

FIELD OF THE INVENTION

This invention relates to a stable biocide composition to be used for inhibiting deterioration or contamination of industrial products or materials, in particular latex emulsions, water base paints, metal processing oils, starch paste, paper coating compositions, textile processing oils, lignin preparations and the like, due to microorganisms, or for preventing slime-related troubles caused by microorganisms in papermaking processes or in factory cooling water systems.

BACKGROUND OF THE INVENTION

In industrial products or materials, such as latex emulsions, water base paints, paper coating compositions, textile oils, metal processing oils and electric insulator materials, in paper and pulp industries and in cooling water systems in various industries, troublesome microorganisms, such as bacteria, fungi and yeasts, can readily grow and cause quality deterioration, for example, decay, change in quality or contamination, of products, or productivity reduction due to slime formation. To prevent the growth of, or control, such troublesome microorganisms, a variety of agents, for example, organometallic compounds, organosulfur compounds, quaternary ammonium compounds and phenolic compounds, have been used so far. However, such compounds have disadvantages; for example, they have toxicity or environmental pollution problems or cause foaming or product quality deterioration in some specific instances. When evaluated as biocides for industrial use, they are not fully satisfactory from the efficacy viewpoint; they are not so effective against certain kinds of microorganism or their efficacy cannot last for long.

To solve such problems encountered with the conventional agents, such as mentioned above, the present inventor has already proposed that a mixture of 5-chloro-2-methyl-3-isothiazolone and 2-methyl-3-isothiazolone (hereinafter referred to as "isothiazolone mixture") should be added, in the metal complex form, to water systems, together with 4,5-dichloro-1,2-dithiol-3-one, to thereby achieve effective slime control (Japanese Kokai Tokkyo Koho No. 1105/1985).

This proposal was based on the finding that the combined use of the active ingredients mentioned above can produce a remarkable synergistic effect. Regrettably, however, the isothiazolone mixture in the metal complex form, one of the active ingredients to be used combinedly, is available only in the form of a complex with an alkaline earth metal compound, such as magnesium chloride, and in the form of an aqueous solution containing magnesium (II) nitrate, which serves as a stabilizer, and, in addition, the other active ingredient, namely, 4,5-dichloro-1,2-dithiol-3-one, is fairly unstable in the presence of water, undergoing hydrolysis, which leads to complete loss of its biocidal activity. Furthermore, the additional presence of an alkali metal salt promotes the decomposition of the dithiol compound. It is thus practically impossible to have a stable slime control composition containing the active ingredients mentioned above, namely, 4,5-dichloro-1,2-dithiol-3-one and the isothiazolone mixture in the metal complex form. Accordingly, in practical application, it is necessary to add combinedly two preparations containing the respective ingredients singly to treatment targets. Such manner of handling a biocidal composition is disadvantageous or troublesome. In addition, in such combined use, the isothiazolone mixture in the metal complex form and the stabilizer magnesium nitrate can cause aggregation of colloidal pitch (resin) in white water in papermaking processes. The resulting adhering resin is a cause of troubles. In spite of its being based on the excellent synergy found with the active ingredients mentioned above, the earlier invention thus has limitations as far as the practical application method and treatment targets are concerned.

SUMMARY OF THE INVENTION

It is an object of the invention to solve the problems mentioned above and provide an excellent biocide composition which has good storage stability and is useful not only as a slime control agent but also in every industrial product or material without producing any adverse effect upon the product treated therewith and in which the excellent synergy of the isothiazolone mixture and 4,5-dichloro-1,2-dithiol-3one in controlling microorganisms is made the most of.

DETAILED DESCRIPTION

As a result of intensive investigations, the present inventor unexpectedly found that a solution of the isothiazolone mixture and 4,5-dichloro-1,2-dithiol-3-one in a substantially anhydrous organic solvent is a biocide composition having good storage stability in spite of the description given in U.S. Pat. No. 3,870,795 to the effect that the isothiazolone mixture is readily decomposed in water or polar organic solvents.

Both the components of the isothiazolone mixture to be used in accordance with the invention, namely, 5-chloro-2-methyl-3-isothiazolone and 2-methyl-3-isothiazolone, have antimicrobial activity. Among them, 5-chloro-2-methyl-3-isothiazolone has very good biocidal activity. It is supposed that 2-methyl-3-isothiazolone serves as an auxiliary to the 5-chloro compound. The mixing ratio between these isothiazolone compounds may optionally be varied by varying the synthesis reaction conditions. From the efficacy and storage viewpoints, however, said ratio should preferably be within the range of 9:1 to 1:9, more preferably 5:1 to 1:5, on the weight basis. The weight ratio between the isothiazolone mixture and 4,5-dichloro-1,2-dithiol-3-one should preferably be within the range of 1:19 to 19:1 when the synergistic effect on microorganisms and the storage stability of the composition are taken into consideration.

As the organic solvent, a hydrophilic organic solvent can preferably be used, and there may be mentioned, among others, alcohols, such as isopropyl alcohol and benzyl alcohol, hydrophilic glycols, such as ethylene glycol, propylene glycol, diethylene glycol, dipropylene glycol, tetramethylene glycol and polypropylene glycol, glycol ethers, such as diethylene glycol monomethyl ether, propylene glycol monomethyl ether, dipropylene glycol monomethyl ether and tripropylene glycol monoethyl ether, and carbonate esters, such as diethyl carbonate and propylene carbonate. Among them, particularly preferred are diethylene glycol monomethyl ether, dipropylene glycol monomethyl ether, diethylene glycol, dipropylene glycol, and mixtures of two or more of these. As necessary, the composition according to the invention may contain a surfactant (nonionic or anionic) and, further, another or other biocides (e.g. 2,2-dibromo-3-nitrilopropionamide, methylenebisthiocyanate, 1,4 bisbromoacetoxybutene-2, 1,2-bisbromoacetoxyethane, 1,2-benzisothiazoline-3-one) and so forth, each in an appropriate amount.

The total content of active ingredients in the composition according to the invention may vary depending on the purpose of use and other factors. Generally, however, the total content of active ingredients should preferably amount to about 0.5–30% by weight based on the whole composition.

The level of addition of the composition according to the invention may vary depending on the object to be treated, the purpose of use and other factors. Generally, when it is applied to industrial products or industrial materials as a preservative or antifungal composition, it should preferably be added thereto in an amount sufficient to give a final total active ingredient concentration of about 0.05–10 ppm. When said composition is used as a slime control agent in papermaking processes, it should preferably be added to white water systems either intermittently 1–3 times a day, each time for a period of 30–60 minutes, at a rate sufficient to give a total active ingredient concentration of about 0.1–20 ppm, or semicontinuously over a period of about 8–12 hours a day to afford a total active ingredient concentration of about 0.01–10 ppm. For use as a slime control agent or algicidal agent in industrial cooling water systems, the composition should preferably be added to said systems at one-week intervals, for instance, in an amount sufficient to give a total active ingredient concentration of 0.05–10 ppm based on the whole amount of water.

The following examples are further illustrative of the present invention. In the examples, 4,5-dichloro-1,2-dithiol-3-one is referred to as "active ingredient (A)", 5-chloro-2-methyl-3-isothiazolone as "active ingredient (B)" and 2-methyl-3-isothiazolone as "active ingredient (C)". The active ingredient (D) used for comparison is a commercial product available under the trademark Kathon WT from Rohm and Haas Company, which is an aqueous solution containing 16.5% of 5-chloro-2-methyl-3-isothiazolone-magnesium chloride, 7.0% of 2-methyl-3-isothiazolone-magnesium chloride and about 13% of magnesium nitrate. Formulations tested The active ingredient (A) was dissolved in each specified solvent composition (Table 1). A surfactant (Tetronic ®702; ethylenediamine-polyoxyethylene/polyoxypropylene adduct) was added as necessary. The active ingredient (B) and (C) or the active ingredient (D) was added to the solution and the resulting mixture was stirred thoroughly to give a liquid formulation. The example formulations tested are summarized in Table 1 and the formulations used for comparison in Table 2. In the tables, "%" means "percent by weight".

TABLE 1

| Ingredients | Examples of the composition according to the invention | | | |
|---|---|---|---|---|
| | Formulation I | Formulation II | Formulation III | Formulation IV |
| Active ingredient (A) | 1.0% | 3.0% | 20.0% | 5.0% |
| Active ingredient (B) | 16.0% | 2.7% | 0.5% | 2.0% |
| Active ingredient (C) | 2.0% | 0.9% | 2.0% | 18.0% |
| Methyl Carbitol | 4.0% | 12.0% | 40.0% | 15.0% |
| Diethylene glycol | 77.0% | — | 35.0% | — |
| Dipropylene glycol | — | 81.2% | — | 59.0% |
| Surfactant (Tetronic 702) | — | 0.2% | 2.5% | 1.0% |

Methyl Carbitol = diethylene glycol monomethyl ether

TABLE 2

| Ingredients | Formulations for comparison | | |
|---|---|---|---|
| | Formulation V | Formulation VI | Formulation VII |
| Active ingredient (A) | 3.0% | 5.0% | 20.0% |
| Active ingredient (D) | 9.5% | 20.0% | 1.0% |
| Methyl Carbitol | 12.0% | 12.0% | 76.5% |
| Diethylene glycol | 75.3% | — | — |
| Dipropylene glycol | — | 63.0% | — |
| Surfactant (Tetronic 702) | 0.2% | — | 2.5% |

EXAMPLE 1

In this example, the formulations I to IV according to the invention and the formulations V to VII for comparison were subjected to stability testing. A 100 g portion of each of the formulations I to VII was placed in a 200 ml mayonaise bottle, which was then capped. The bottle was maintained at 40° C. in a constant-temperature chamber. After the lapse of each specified period, the contents of each bottle were examined for change in appearance and at the same time the change in concentration of each of the active ingredients (A), (B) and (C) was estimated by HPLC (high-performance liquid chromatography) and the percent decomposition was calculated for each active ingredient based on the assay data thus obtained. In the HPLC analysis, benzoic acid was added as an internal standard. The results thus obtained are shown below in Table 3 and Table 4.

TABLE 3

| | Decomposition of each active ingredient in each formulation | | | | | | | | | | | | | | | | | |
|---|---|---|---|---|---|---|---|---|---|---|---|---|---|---|---|---|---|---|
| | Directly after preparation | | | After 7 days | | | After 15 days | | | After 30 days | | | After 60 days | | | After 90 days | | |
| Formulation | A | B | C | A | B | C | A | B | C | A | B | C | A | B | C | A | B | C |
| I | 0 | 0 | 0 | 0 | 0 | 0 | 0 | 0 | 0 | 0 | 0 | 0 | 0 | 5 | 0 | 0 | 10 | 0 |
| II | 0 | 0 | 0 | 0 | 0 | 0 | 0 | 0 | 0 | 0 | 0 | 0 | 0 | 3 | 0 | 0 | 8 | 0 |
| III | 0 | 0 | 0 | 0 | 0 | 0 | 0 | 0 | 0 | 0 | 0 | 0 | 0 | 3 | 0 | 0 | 5 | 0 |
| IV | 0 | 0 | 0 | 0 | 0 | 0 | 0 | 0 | 0 | 0 | 0 | 0 | 0 | 0 | 0 | 0 | 3 | 0 |
| V | 0 | 0 | 0 | 30 | 0 | 0 | 90 | 10 | 0 | 100 | 50 | 0 | 100 | 70 | 0 | 100 | 90 | 10 |
| VI | 0 | 0 | 0 | 90 | 0 | 0 | 100 | 10 | 0 | 100 | 50 | 0 | 100 | 70 | 0 | 100 | 90 | 20 |
| VII | 0 | 0 | 0 | 10 | 0 | 0 | 50 | 5 | 0 | 100 | 40 | 0 | 100 | 50 | 0 | 100 | 80 | 0 |

Note:
Each percent decomposition was calculated based on the peak area ratio relative to the internal standard used in HPLC.

TABLE 4

| Formulation | Changes in formulation appearance | | | | | |
|---|---|---|---|---|---|---|
| | Directly after preparation | After 7 days | After 15 days | After 30 days | After 60 days | After 90 days |
| I | Light-yellow and clear | Light-yellow and clear | Light-yellow and clear | Light-yellow and clear | Light-yellow and clear | yellow and clear |
| II | Light-yellow and clear | Light-yellow and clear | Light-yellow and clear | Light-yellow and clear | Light-yellow and clear | yellow and clear |
| III | Light-yellow and clear | Light-yellow and clear | Light-yellow and clear | Light-yellow and clear | Light-yellow and clear | Light-yellow and clear |
| IV | Light-yellow and clear | Light-yellow and clear | Light-yellow and clear | Light-yellow and clear | Light-yellow and clear | Light-yellow and clear |
| V | Light-yellow and clear | Red and clear | Small amount of precipitate | Large amount of precipitate | Large amount of precipitate | Large amount of precipitate |
| VI | Light-yellow and clear | Red and opaque | Small amount of precipitate | Large amount of precipitate | Large amount of precipitate | Large amount of precipitate |
| VII | Light-yellow and clear | Reddish brown and clear | Red and opaque | Large amount of precipitate | Large amount of precipitate | Large amount of precipitate |

Note:
For formulations V–VII, decomposition gas formation was observed after 30 days of storage at 40° C.

EXAMPLE 2

The formulation II prepared in accordance with the invention was examined for preservative and other effects on a synthetic polymer emulsion. For comparison, formulations (VIII and IX) respectively containing the active ingredients (A) and (D) singly and having the compositions given below were prepared and tested, together with the formulation V.

| Formulation VIII | | Formulation IX | |
|---|---|---|---|
| Active ingredient (A) | 10% | Active ingredient (D) | 20% |
| Methyl carbitol | 40% | Dipropylene glycol | 70% |
| Diethylene glycol | 49% | Water | 10% |
| Surfactant (Tetronic 702) | 1% | | |

A 10% aqueous dilution of each formulation was added, at a specified addition level (1,000 ppm), to 100 ml of a styrenebutadiene latex having a pH of 7. After gentle stirring, the mixture was allowed to stand for 5 minutes and then filtered using a 100 mesh wire gauze. The quantity of a residue resulting from latex coagulation remaining on the wire gauze, if any, was estimated by the eye. The filtrate was placed in a mayonaise bottle and, after capping, allowed to stand outdoors, and viable microbial cells were counted at timed intervals. The results obtained are shown in Table 5.

TABLE 5

| Formulation | Influences on latex and preservative effects | | | | | |
|---|---|---|---|---|---|---|
| | Addition level (ppm) | Coagulation product on wire gauze | Viable cell count (cells/ml) | | | |
| | | | After 1 day | After 10 days* | After 20 days | After 30 days |
| None | | Absent | $3.8 \times 10^4$ | $2.2 \times 10^6$ | $8.6 \times 10^7$ | $>10^8$ |
| II | 1000 | Absent | $<10^2$ | $<10^2$ | $<10^2$ | $<10^2$ |
| V | 1000 | Plenty | $<10^2$ | $<10^2$ | $<10^2$ | $4.5 \times 10^3$ |
| VIII | 1000 | Absent | $<10^2$ | $<10^2$ | $6.8 \times 10^5$ | $2.0 \times 10^7$ |
| IX | 1000 | Plenty | $5.0 \times 10^3$ | $<10^2$ | $5.0 \times 10^4$ | $3.2 \times 10^6$ |

Note:
The asterisk (*) means that, after viable cell counting after 10 days of standing, the sample with no formulation added (after 10 days of standing) was added to each sample with one of the formulations added, in an amount of 10%, and the test was continued.

As shown in Table 5, the above-mentioned formulation II according to the invention showed a good preservative performance without producing any adverse effect on the latex. A preservative performance was observed also with the formulation V for comparison but said formulation had a problem from the practical viewpoint in that it caused formation of a latex coagulation product. The single active ingredient formulations VIII and IX were disadvantageous from the preservative performance and coagulation product formation viewpoints, among others.

EXAMPLE 3

In a certain paper mill, the same formulation II of the invention as used in Example 2 was added to the white water pit in the papermaking process for 8 hours a day in a dose sufficient to give a concentration in water of 10 ppm. After 14 days of continuous operation, the machine was washed and papermaking was further continued for 14 days while adding the formulation V in the same manner as above. The number of paper breaks during each operation period and the number of pitch stains on the paper products obtained on the 13th day in each period were examined. The results are shown in Table 6.

TABLE 6

| Formulation | Paper mill test results | |
|---|---|---|
| | Number of paper breaks (for 14 days of operation) | Number of pitch stains (stains/m²) |
| II | 1 | 0 |
| V | 3 | 10 |

As shown in Table 6, the formulation according to the invention reduced the number of slime troubles, improved the productivity and solved the problem of pitch-caused product quality deterioration.

In accordance with the invention, a biocide composition having good storage stability can be obtained by dissolving a biocide combination of the isothiazolone mixture and 4,5-dichloro-1,2-dithiol-3-one in a substantially anhydrous organic solvent and, accordingly, a useful biocide composition for industrial use can be provided in which the synergistic effect on microorganisms resulting from the combined use of both the active ingredients is made the best of and which is not only useful as a slime control agent but also usable in substantially all kinds of industrial products or industrial materials without producing any adverse effect thereon.

While the present invention has been described by the foregoing specification including examples, the embodiments described herein can be changed and modified in various manners within the scope and the spirit of this invention.

What is claimed is:

1. A stable biocide composition for industrial use which comprises 4,5-dichloro-1,2-dithiol-3-one and a mixture of 5-chloro-2-methyl-3-isothiazolone and 2-methyl-3-isothiazolone, together with a substantially anhydrous organic solvent for dissolving 4,5-dichloro-1,2-dithiol-3-one and said mixture of 5-chloro-2-methyl-3-isothiazolone and 2-methyl-3-isothiazolone.

2. A stable biocide composition as claimed in claim 1, wherein the weight ratio between 5-chloro-2-methyl-3-isothiazolone and 2-methyl-3-isothiazolone is within the range of 9:1 to 1:9.

3. A stable biocide composition as claimed in claim 1, wherein the weight ratio between 4,5-dichloro-1,2-dithiol-3-one and the mixture of 5-chloro-2-methyl-3-isothiazolone and 2-methyl-3-isothiazolone is within the range of 1:19 to 19:1.

4. A stable biocide composition as claimed in claim 1, wherein the organic solvent is a hydrophilic organic solvent.

5. A stable biocide composition as claimed in claim 1 or 4, wherein the organic solvent is selected from the group consisting of alcohols, hydrophilic glycols, glycol ethers, carbonate esters, and mixtures of two or more of these.

* * * * *